United States Patent [19]

Norenburg

[11] Patent Number: 4,496,381

[45] Date of Patent: Jan. 29, 1985

[54] APPARATUS AND METHOD FOR RECOVERING LIGHT HYDROCARBONS FROM HYDROGEN CONTAINING GASES

[75] Inventor: Johannes Norenburg, Marblehead, Mass.

[73] Assignee: Stone & Webster Engineering Corp., Boston, Mass.

[21] Appl. No.: 462,982

[22] Filed: Feb. 1, 1983

[51] Int. Cl.³ .............................................. F25J 3/02
[52] U.S. Cl. ......................................... 62/30; 62/31; 62/34; 62/39
[58] Field of Search .................. 62/24, 27, 28, 29, 30, 62/31, 32, 34, 38, 39, 42, 43, 44, 40; 208/347, 350, 351, 352, 354; 585/800

[56] References Cited

U.S. PATENT DOCUMENTS

| | | | |
|---|---|---|---|
| 3,675,435 | 7/1972 | Jackson et al. | 62/39 |
| 3,729,944 | 5/1973 | Kelley et al. | 62/39 |
| 4,002,042 | 1/1977 | Pryor et al. | 62/28 |

*Primary Examiner*—Frank Sever
*Attorney, Agent, or Firm*—Hedman, Gibson, Costigan & Hoare

[57] ABSTRACT

A process and apparatus provide enhanced recovery of ethylene, hydrogen and methane from the effluent produced by cracking olefins. A cracked gas is fractionally condensed in several stages. The overhead vapor from the last stage is refluxed in a rectifier tower to enable recovery of residual light hydrocarbons such as ethylene in the cracked gas and for improving the purity and yield of hydrogen. The refrigeration for producing the reflux is obtained by expanding a portion of the overhead vapor from the rectifier tower. Preferably, the fractional condensates of the cracked gas and the ethylene rich bottoms product from the rectifier tower are directed to a demethanizer. The overhead vapor from the demethanizer can be directed to the rectifier tower for recovery of ethylene contained therein.

18 Claims, 2 Drawing Figures

APPARATUS AND METHOD FOR RECOVERING LIGHT HYDROCARBONS FROM HYDROGEN CONTAINING GASES

This invention relates to devices and methods for enhancing the recovery of light hydrocarbons from hydrogen containing gases. More particularly, the invention relates to apparatus and processes that will increase the recovery of ethylene and hydrogen, and will improve the purity of the hydrogen recovered from cracked light hydrocarbon gases.

BACKGROUND OF THE INVENTION

A pyrolysis or similar unit for the production of ethylene yields a cracked gas which is fractionally condensed in one or more stages. Each stage produces an overhead vapor and a liquid fraction. The overhead vapors from each stage are directed to the subsequent stages, while the liquid fractions are directed to other processing units. For example, the liquid fractions may be fed to a multi-feed demethanizer tower which produces a liquid having large proportions of ethylene and an overhead vapor having large proportions of methane and a smaller amount of residual ethylene.

The overhead vapor from the last stage of the fractional condensers is a gas that is rich in hydrogen and methane and contains significant amounts of ethylene. This overhead vapor from the last stage of the fractional condensers has been used to cool other parts of this or related systems. In other applications, the overhead vapor from the last stage has been further separated into its main components of hydrogen and methane. Both of these optional treatments for the overhead vapor are referred to, for example, in U.S. Pat. No. 4,002,042.

The prior art systems of the type described above have been deficient in certain respects. First, the ethylene included in the overhead vapor from the last stage of the fractional condensers is for all practical purposes wasted. Consequently, the recovery of ethylene by the total system is lower than desired. Second, the ethylene in the overhead vapor from the last stage of the fractional condensers affects the purity of the hydrogen obtained in any subsequent separation steps. To obtain a purer quality of hydrogen requires more complex equipment which operates at an increased cost. Additionally, in some systems, steps that provide purer hydrogen result in a lower yield of hydrogen.

SUMMARY OF THE INVENTION

In view of the deficiencies of the prior art hydrocarbon cracking and fractional condensing systems, it is an object of the present invention to provide an apparatus and method for achieving an increased recovery of ethylene.

It is another object of the subject invention to provide an apparatus and method to afford an increased recovery of hydrogen from a hydrocarbon cracking system.

It is an additional object of the subject invention to provide an apparatus and process which enable a yield of hydrogen having enhanced purity from a hydrocarbon cracking system.

It is a further object of the subject invention to provide an apparatus and process which makes efficient use of expansion work available from the overhead vapor of a fractional condenser.

The subject invention is especially effective for use with cracked gases that are fractionally condensed in several stages. More particularly, the subject invention is especially effective for use with cracked gases that have a high ratio of hydrogen to methane, such as those that are derived from cracking ethane. These cracked gases, for example, could be derived from a pyrolysis unit used to produce ethylene.

In a system of this type, the cracked gases are fractionally condensed in several stages, and the liquid fraction derived at each stage is fed to a conventional multi-feed demethanizer tower. The overhead vapor from each stage is fed to the next stage with the result that the last stage produces an overhead vapor that is rich in hydrogen and methane and which also includes significant amounts of ethylene.

The subject invention enables increased recovery of ethylene and hydrogen and improved hydrogen purity. This recovery of ethylene and hydrogen is achieved in part by relying upon the expansion work that is available from the high pressure and low temperature gases and liquids present in the system. More particularly, the subject invention directs the hydrogen rich vapor from the last stage of the fractional condensers to an overhead rectifier where the residual ethylene in the vapor entering the rectifier is recovered. The rectifier tower is refluxed by one portion of residual gases from the rectifier This reflux has been refrigerated by the expansion of a second portion of the residual gases from the rectifier.

To achieve this reflux, an overhead fraction including hydrogen, methane and a small amount of ethylene is withdrawn from the rectifier and is cooled in several stages. The last stage produces a condensate of pure methane and an overhead stream of essentially hydrogen. Both the hydrogen and methane streams are expanded, and are passed in heat exchange relationship with the overhead vapor from the rectifier, thereby enabling a portion of the overhead from the rectifier to be used as reflux. This reflux causes the overhead stream from the rectifier to be low in ethylene, and generates a rectifier bottom product that is rich in ethylene. As a result of this unique assembly and process, the recovery of both hydrogen and ethylene are substantially increased. Additionally, the hydrogen produced is significantly more pure than the hydrogen obtained from prior art systems at comparable cost.

The subject apparatus and process may be modified to direct the overhead vapor from the demethanizer to the rectifier tower. This enables the rectifier tower to be operated at a lower pressure and also improves the efficiency of the demethanizer.

DETAILED DESCRIPTION OF THE PREFERRED EMBODIMENT

Figure 1:
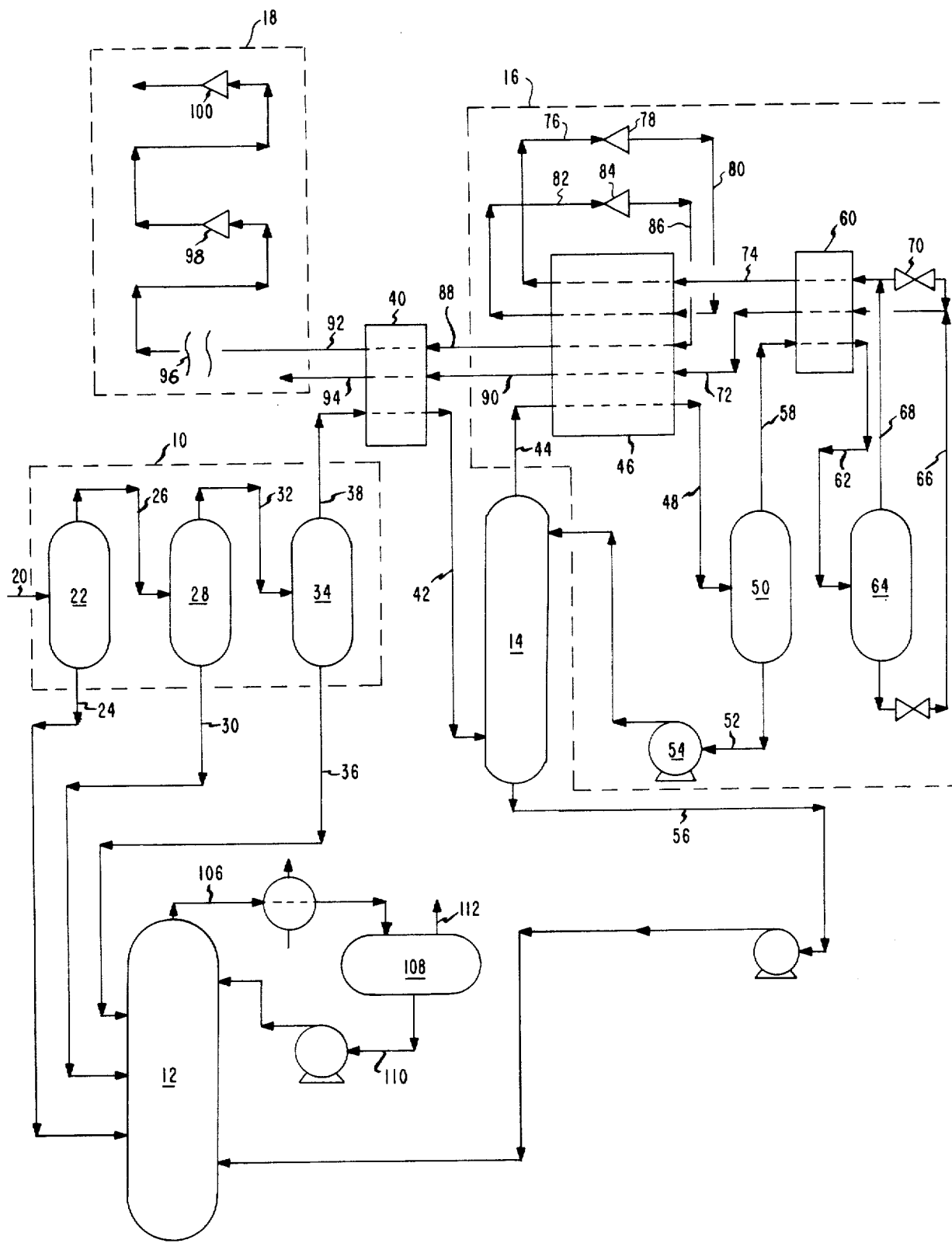
FIG. 1 is a schematic drawing of the apparatus of the subject invention.

The apparatus of the subject invention, as illustrated in FIG. 1, is designed to provide an increased recovery of ethylene from cracked gases. As mentioned previously, the subject apparatus is particularly effective for cracked gases with a high ratio of hydrogen to methane, such as gases that are derived from the cracking of ethane.

The apparatus shown in FIG. 1 includes a fractional condenser system 10, a demethanizer 12, a rectifier tower 14, a refrigeration system 16 and a product gas system 18. Briefly, the fractional condenser system 10 defines an enclosed system which fractionally condenses cracked gas from a pyrolysis unit in several stages. Each stage of the fractional condenser system 10 produces a liquid fraction which is directed out of the system, and the last stage of the fractional condenser system 10 produces a hydrogen rich vapor which also is directed out of the fractional condenser system 10. The liquid fractions from the fractional condenser system 10 all are directed to a demethanizer 12. These liquid fractions are treated in the demethanizer 12 to recover the desired light hydrocarbon product such as ethylene.

The hydrogen rich vapor from the last stage of the fractional condenser system 10 is directed to the rectifier tower 14. The rectifier tower 14 is refluxed by a portion of the residual gases from the rectifier tower 14 that have been condensed and separated in the refrigeration system 16. This reflux in the rectifier tower 14 yields a bottoms product substantially rich in ethylene which is directed to the demethanizer 12. The portion of the overhead vapor from the rectifier tower 14 that is not used as reflux is substantially separated into its major components of methane and hydrogen in the refrigeration system 16. The hydrogen and methane are expanded in the refrigeration system 16, thereby providing the necessary refrigeration for the reflux in the rectifier tower 14. The hydrogen and methane that are derived in the refrigeration system 16 by separating the overhead residual vapor from rectifier tower 14 are directed from the refrigeration system 16 to a product gas system 18 for use in other chemical processes or as fuel.

Referring to the fractional condenser system 10 of FIG. 1 in greater detail, a cracked gas from a pyrolysis unit (not shown) is directed through a cracked gas line 20 to the first stage 22 of the fractional condenser system 10. A liquid fraction is directed from the first stage 22 as a bottom product through the first liquid fraction line 24 to the demethanizer 12. In a system for cracking ethane to produce ethylene, the liquid fraction from the first stage 22 enters the demethanizer 12 through the first stage liquid line 24 at a temperature of approximately $-25°$ F. to $-35°$ F.

The overhead vapor from the first stage 22 is directed through the first stage vapor line 26 into the second stage 28 of the fractional condenser system 10. In a manner similar to that described for the first stage 22, the liquid fraction from the second stage 28 is directed through the second stage liquid line 30 into the demethanizer 12. The liquid fraction from the second stage liquid line 30, enters the demethanizer 12 at a lower temperature than the liquid fraction from the first stage 22. In the system described above, the liquid fraction directed into the demethanizer 12 through the second stage liquid line 30 would be at a temperature of approximately $-89°$ F.

The overhead vapor from the second stage 28 of the fractional condenser system 10 is directed through the second stage vapor line 32 into the final stage 34. The liquid fraction from the final stage 34 is directed through the final stage liquid line 36 into the demethanizer 12, and enters the demethanizer 12 at a temperature of about $-144°$ F. for the system described above. The pressure in the final stage 34 of the fractional condenser system 10 is approximately 418 psia.

The overhead vapor from the last stage 34 of the fractional condenser system 10 is directed through the final stage vapor line 38 to the final stage heat exchanger 40. This overhead vapor from the last stage 34 will be rich in hydrogen and methane and includes significant amounts of ethylene. The final stage heat exchanger 40 causes this vapor from the fractional condenser system 10 to be lowered in temperature from approximately $-145°$ F. to approximately $-175°$ F. The cooled and partially condensed vapor from the fractional condenser system 10 then is directed from the final stage heat exchanger 40 through the rectifier feed line 42 and into the rectifier tower 14.

The rectifier tower 14, as explained above, is in communication with the fractional condenser system 10 so as to receive a vapor containing large amounts of hydrogen and methane and significant amounts of ethylene. The rectifier tower 14 also is in communication with the refrigeration system 16 which provides a reflux for the rectifier tower 14, and with the demethanizer 12. The reflux causes a more complete recovery of ethylene in the rectifier tower 14 as a bottoms product which then is directed to the demethanizer 12 for further processing. The reflux also reduces the ethylene that would be wasted in the overhead of the rectifier tower 14 and thus the hydrogen recovered from this overhead is purer. The pressure within the rectifier tower 14 preferably will be approximately 450 psia for the embodiment shown in FIG. 1

The overhead vapor from the rectifier tower 14 is directed to the refrigeration system 16 through the rectifier vapor line 44. More particularly, the overhead vapor leaves the rectifier tower 14, and is directed through the rectifier vapor line 44 into the hot side of an expansion heat exchanger 46. As explained in greater detail below, the refrigeration for the expansion heat exchanger 46 is provided by expanding a portion of the overhead vapor.

The overhead product from the rectifier tower 14 that has been cooled in the expansion heat exchanger 46 then is directed through the refrigerated rectifier vapor line 48 and into the reflux separator 50. The reflux separator 50 produces a reflux which is directed through a reflux line 52 and is urged by a reflux pump 54 into the rectifier tower 14. The reflux entering the rectifier tower 14 produces an ethylene rich condensate which is directed from the rectifier tower 14 through the rectifier bottom line 56 and ultimately to the demethanizer 12.

Returning to the refrigeration system 16, the reflux separator 50 produces a hydrogen rich vapor with approximately 25% methane which is directed from the reflux separator 50 through the overhead separator line 58 and into the hydrogen/methane heat exchanger 60 where it is cooled. As explained further below, the refrigeration for the hydrogen/methane heat exchanger 60 is obtained by first separating and then expanding the methane in the hydrogen rich vapor derived from the reflux separator 50. This cooled product from the hydrogen/methane heat exchanger 60 then is directed through the methane separator feed line 62 and into the methane separator 64. The methane separator 64 produces a pure liquid methane bottom product and an overhead vapor of approximately 90% hydrogen. The pure methane is directed from the methane separator 64 through the methane line 66 where it is expanded and cooled. The hydrogen rich overhead product from the methane separator 64 is directed from the methane separator 64 through the hydrogen line 68. The methane and hydrogen are directed through the methane and hydrogen lines 66 and 68 respectively and into tne hydrogen methane indirect heat exchanger 60, to provide refrigeration for the overhead vapor product from the reflux separator 50 as explained above. If necessary, a small and controlled amount of hydrogen is directed through a valve 70, and is mixed with the pure methane in the methane line 66. This mixture of the hydrogen with the methane in the methane line 66 is necessary under certain conditions of plant fuel gas pressure, pressure in methane line 66 and the required hydrogen purity to provide an adequate temperature difference at the cold end of the hydrogen/methane heat exchanger 60. The heat exchange between the hydrogen and methane lines 66 and 68, on the one hand, and the overhead product from the reflux separator on the other hand increases the temperature of the hydrogen and methane.

The methane rich product is directed from the hydrogen/methane heat exchanger 60 through the second methane line 72 and into the expansion heat exchanger 46, where the temperature of the methane rich product is increased by heat exchange with the overhead vapor from the rectifier tower 14.

The hydrogen rich product from the hydrogen/methane heat exchanger 60 is directed through the second hydrgen line 74 and into the cold side of the expansion heat exchanger 46, where through indirect heat exchange with the overhead product from the rectifier tower 14, the temperature of the hydrogen rich product is increased. The hydrogen rich product then is directed from the expansion heat exchanger 46 through the first expansion turbine feed line 76 and into the first expansion turbine 78. The first expansion turbine 78 expands the hydrogen rich product and thereby decreases its temperature. The hydrogen rich product then is directed through the first expansion turbine recirculation line 80 back into the expansion heat exchanger 46 for additional heat exchange with the overhead vapor from the rectifier tower 14. In the manner explained above, this heat exchange causes the hydrogen rich product directed into the expansion heat exchanger 46 through the first expansion turbine recirculation line 80 to be increased in temperature. The hydrogen rich product next is directed through the second expansion turbine feed line 82 and into the second expansion turbine 84 where the hydrogen rich product again is expanded to a lower temperature. The expanded and cooled hydrogen rich product then is directed through the second expansion turbine recirculation line 86 into the expansion heat exchanger 46 for additional heat exchange with the overhead vapor from the rectifier tower 14. As discussed previously, this multiple heat exchange relationship which takes place in the expansion heat exchanger 46 causes the overhead vapor from the rectifier tower 14 to be cooled and partially condensed, thereby enabling the condensed part to be separated in the reflux separator 50.

The methane and hydrogen rich products are directed from the expansion heat exchanger 46 through the third hydrogen and third methane lines 88 and 90 which direct the respective products into the final stage heat exchanger 40, where through heat exchange relationship they reduce the temperature of the vapor product passing from the fractional condenser system 10 to the rectifier tower 14. The hydrogen and methane rich vapor products leave the final stage heat exchanger 40 and are directed into the product gas system 18 through the hydrogen and methane product gas lines 92 and 94. The specific processes to take place in the product gas system 18 will vary according to the needs of the overall operation. Typically however, both the hydrogen and methane rich products are directed into a heat exchanger for useful refrigeration purposes, as indicated by heat exchange unit 96. The hydrogen rich product typically then is compressed as shown by compression turbines 98 and 100 and then directed to further processing. The compression turbines 98 and 100 can be driven by expansion turbines 78 and 84.

Turning to the demethanizer 12, the ethylene rich bottom product of the rectifier tower 14 is directed through the rectifier bottom line 56 and to the demethanizer 12. The overhead product of the demethanizer 12 which is substantially rich in hydrogen and methane is directed from the demethanizer 12 through the demethanizer overhead line 106 and into the reflux drum 108. Preferably, this overhead product from the demethanizer 12 is passed in a heat exchange relationship with a $C_2$- refrigerant. The reflux from the reflux drum is directed through the demethanizer reflux line 106 and back to the demethanizer 12. The overhead vapor product from the reflux drum 108 can become a tail gas which is directed to further processing, or as explained below can be further directed to the rectifier tower 14 for recovery of additional ethylene.

Figure 2:
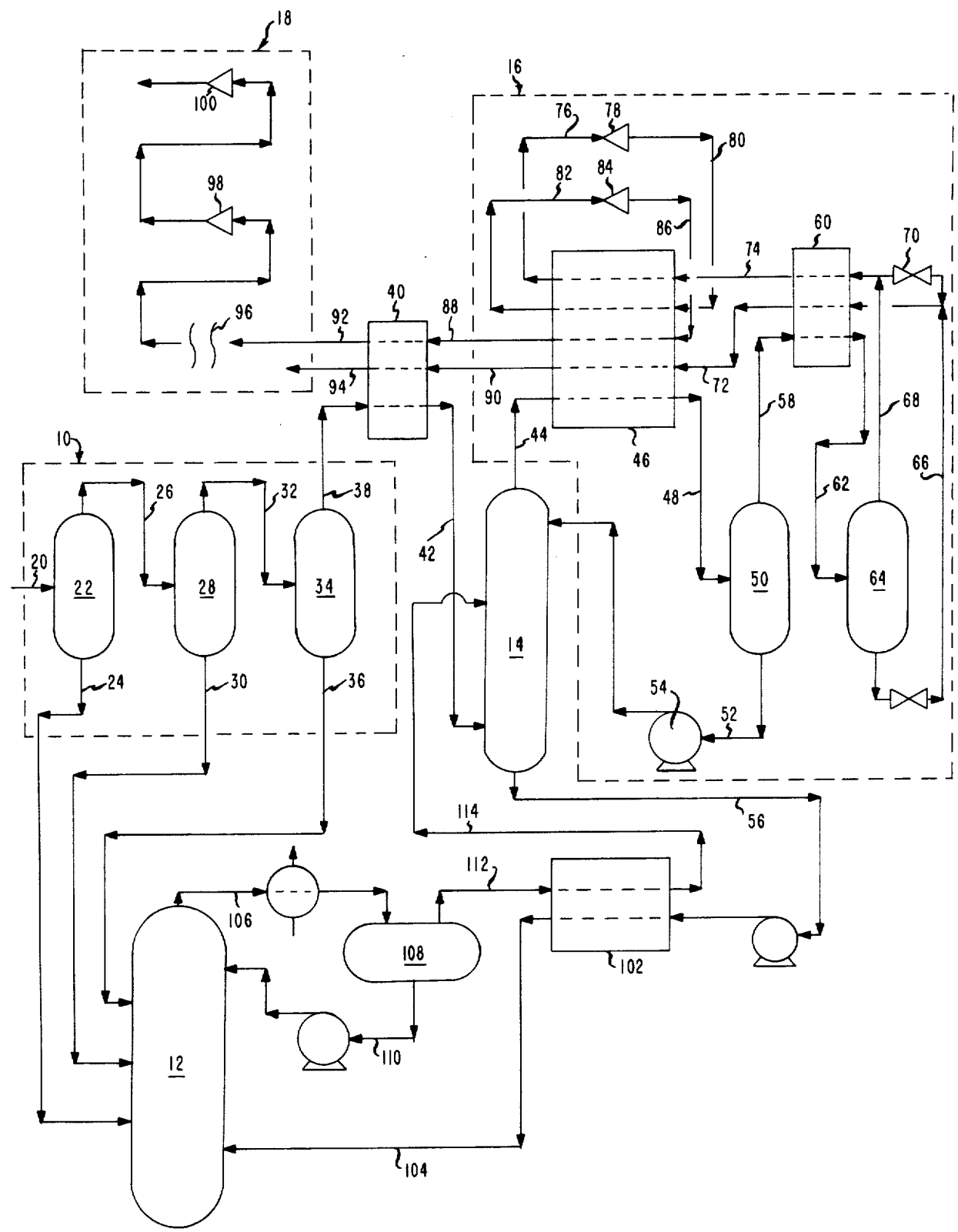
FIG. 2 is a schematic drawing of an embodiment of the subject invention wherein the overhead vapor from the demethanizer is directed to the rectifier tower.

Turning to FIG. 2, the system described above has been modified to recover the residual ethylene in the overhead vapor from the demethanizer. Specifically, the overhead vapor from the reflux drum 108 is directed through line 112 to heat exchanger 102 where it is cooled to about −151° F. by heat exchange with the ethylene rich bottoms product from rectifier tower 14 that has been directed through the rectifier bottom line 56. This heat exchange also raises the temperature of the ethylene rich bottoms product to about −152° F. as it is directed through the demethanizer feed line 104 to the demethanizer 12. The cooled overhead vapor from the reflux drum 108 then is directed through the second rectifier feed line 114 to the rectifier tower 14 where residual ethylene is recovered. This system, as shown in FIG. 2, enables an increased recovery of ethylene, and also enables the rectifier tower 14 to operate at approximately 392 psia rather than the approximately 450 psia required for the system shown in FIG. 1.

Operation of the system described with reference to FIG. 2 in conjunction with a pyrolysis unit for cracking a fresh feed of 250,000 pounds per hour of a mixture of approximately 70% (LV) ethane and 30% (LV) propane will result in approximately 170 million cubic feet per day of cracked effluent to be directed into the fractional condenser system 10. This cracked effluent would be at a temperature of approximately 55° F. and would be of approximately the following composition:

|  | Mole % |
| --- | --- |
| Hydrogen | 30 |
| Methane | 12 |
| Ethylene | 33 |
| Ethane | 20 |
| Propylene | 3 |
| Propane | 2 |

The overhead vapor from the final stage 34 of the fractional condenser system 10 would leave the fractional condenser system 10 at a rate of approximately 64 million cubic feet per day. This overhead vapor from the fractional condenser system 10 would be at approximately −144° F. and would be of approximately the following composition:

|  | Mole % |
|---|---|
| Hydrogen | 77 |
| Methane | 18 |
| Ethylene and heavier | 5 |

The overhead vapor from the fractional condenser system 10 would be directed to the rectifier tower 14. The rectifier tower 14 also would receive the overhead vapor from the demethanizer 12 for the system described with reference to FIG. 2. This overhead vapor from the demethanizer 12 would flow to the rectifier tower 14 at a rate of approximately 12 million cubic feet per day. This overhead vapor from the demethanizer 12 would enter the rectifier tower 14 at a temperature of approximately −151° F. and would be of approximately the following composition:

|  | Mole % |
|---|---|
| Hydrogen | 16 |
| Methane | 81 |
| Ethylene | 3 |

Under the conditions described above, the rectifier tower 14 would operate at a pressure of approximately 392 psia. The rectifier tower 14 would produce an overhead vapor at a rate of approximately 80 million cubic feet per day and a temperature of approximately −203° F. This overhead vapor from the rectifier tower 14 would have the following approximate composition:

|  | Mole % |
|---|---|
| Hydrogen | 65 |
| Methane | 35 |
| Ethylene | less than 0.1 |

The cooling of the overhead vapor from the rectifier tower 14 in the expansion heat exchanger 46 would require an expenditure of about 3,070,000 BTU/hr. of the available expansion work, and would cool this overhead vapor to about −212° F. The cooling of the overhead vapor from the rectifier tower 14 in the expansion heat exchanger 46 would partially condense the overhead vapor. The condensate portion of the partially condensed overhead vapor from the rectifier tower 14 would be separated in the reflux separator 50 to yield a reflux condensate which would flow at a rate of approximately 78 GPM and would have a composition of approximately:

|  | Mole % |
|---|---|
| Hydrogen | 3 |
| Methane | 97 |
| Ethylene | less than 0.1 |

The portion of the overhead vapor from the rectifier tower 14 that is not condensed would leave the reflux separator 50 as an overhead product. This overhead product from the reflux separator 50 would flow at a rate of approximately 71 million cubic feet per day and would have a composition of approximately 75% hydrogen and 25% methane. The cooling of this hydrogen rich vapor to about −245° F. in the hydrogen/methane heat exchanger 60 will require approximately 6,440,000 BTU/hr. As explained previously, the hydrogen line 68 would carry a gas containing about 90 mole percent hydrogen. Part of this gas would be directed through valve 70 and would be mixed with the pure methane. The resulting mixture would include about 10 to 15 mole percent hydrogen. Multiple recirculation of the hydrogen through the expansion turbines 78 and 84 to provide cooling for the expansion heat exchanger 46 would require a total of about 890 HP in the expansion turbines 78 and 84. This part of the apparatus would yield a hydrogen rich product at a rate of approximately 54 million cubic feet per day at −207° F. and 130 psia. This gas would have a composition of approximately:

|  | Mole % |
|---|---|
| Hydrogen | 90 |
| Methane | 10 |
| Ethylene | — |

The methane rich gas leaving the expansion heat exchanger flow at a rate of approximately 17 million cubic feet per day at a temperature of approximately −207° F. and 130 psia. This methane rich gas would have an approximate composition of:

|  | Mole % |
|---|---|
| Hydrogen | 15 |
| Methane | 85 |
| Ethylene | — |

The rectifier tower 14 would produce an ethylene rich bottoms product which would leave the rectifier tower 14 at a rate of approximately 15,000 pounds per hour and a temperature of approximately −187° F. This bottoms product from the rectifier tower 14 would have an approximate composition of:

|  | Mole % |
|---|---|
| Hydrogen | 1 |
| Methane | 40 |
| Ethylene | 50 |
| Ethane | 9 |

What is claimed is:

1. An apparatus comprising: elements designed, dimensioned and arranged for recovering ethylene from a cracked gas containing ethylene, methane and hydrogen, said apparatus including,
   (a) a rectifier tower through which the cracked gas passes;
   (b) an overhead line extending from the rectifier tower;
   (c) a refrigeration system in communication with the rectifier tower, said refrigeration system comprising:
   indirection heat exchange means in communication with said rectifier tower for cooling and partially condensing an overhead vapor passing from said rectifier tower overhead line through the hot side of said indirect heat exchange means; an expansion means in communication with said heat exchange means for expanding the non-condensed portion of the partially condensed overhead vapor discharged from the hot side of the heat exchange means and recirculating said non-condensed portion to the cold side of said indirect heat exchange means for refrigeration; and (d) a reflux means in communication with the hot side of said indirect heat exchange means and said rectifier tower for directing the condensed portion of the partially condensed rectifier tower overhead vapor from the hot side of the heat exchange means to the rectifier tower for reflux, thereby producing an ethylene rich bottoms product from said rectifier tower.

2. An apparatus as in claim 1 further comprising a demethanizer in communication with said rectifier tower for recovering the ethylene from the ethylene rich bottoms product of said rectifier tower.

3. An apparatus as in claim 2 wherein said demethanizer tower includes an overhead line in communication with said rectifier tower for directing overhead vapor from said demethanizer to said rectifier tower, whereby the ethylene in the overhead vapor from the demethanizer is recovered in the rectifier tower.

4. An apparatus as in claim 1 wherein the source of the cracked gas is a pyrolysis unit for cracking ethane and further comprising a fractional condenser system between the pyrolysis unit and the rectifier tower, said fractional condenser system separating the cracked effluent from the pyrolysis unit into a liquid fraction and an ethylene containing overhead vapor product which is directed to said rectifer tower and a demethanizer into which said liquid fraction from the fractional condenser system is delivered for the recovery of ethylene.

5. An apparatus as in claim 4 further comprising means for providing communication between said demethanizer and said rectifier tower for delivery of bottoms product from said rectifier tower to said demethanizer, and for delivery of the overhead product from said demethanizer to said rectifier tower for recovering the ethylene therein.

6. An apparatus as in claim 1 wherein the overhead vapor directed through said rectifier tower overhead line comprises hydrogen, methane and ethylene.

7. An apparatus as in claim 1 wherein said ethylene containing gas is a vapor fraction of cracked ethane.

8. A method for recovering ethylene from a cracked gas comprised of ethylene, methane and hydrogen comprising the steps of:
(a) directing a stream of the cracked gas to a rectifier tower;
(b) removing an overhead vapor from said rectifier tower;
(c) directing the overhead vapor from said rectifier tower through the hot side of an indirect heat exchanger;
(d) cooling and partially condensing said overhead vapor in the hot side of said heat exchanger;
(e) expanding and recirculating the non-condensed portion of the overhead vapor to the cold side of the indirect heat exchanger;
(f) refluxing the rectifier tower with the condensed portion of the overhead vapor; and
(g) recovering ethylene as a bottoms product from said rectifier tower.

9. A method as in claim 8, further comprising the steps of:
directing the bottoms product from the rectifier tower to a demethanizer;
processing the bottoms product from the rectifier tower in the demethanizer to produce an overhead vapor containing residual ethylene; and
directing the overhead vapor from the demethanizer to the rectifier tower to recover the residual ethylene therein.

10. A process as in claim 9 further comprising the steps of:
directing the ethylene rich liquid fraction from the fractional condenser system to a demethanizer; and
delivering the bottoms product from the rectifier to the demethanizer whereby over 99 percent of the ethylene is recovered in the demethanizer.

11. A method as in claim 8 wherein the ethylene containing gas is provided by
cracking ethane and further comprising the steps of fractionally condensing the cracked ethane serially in several stages to provide a vapor fraction of ethylene containing gas and an ethylene rich liquid fraction, and delivering the vapor fraction to the rectifier tower.

12. A method as in claim 8 wherein the non-condensed portion of the overhead vapor from the rectifier tower comprises hydrogen and methane.

13. A method as in claim 8 further comprising the steps of:
(a) expanding and cooling the noncondensed portion of the rectifier tower overhead vapor from the hot side of the heat exchanger and
(c) circulating the expanded and cooled non-condensed portion of the rectifier tower overhead from the expansion turbine through the cold side of the heat exchanger.

14. A process as in claim 8 further comprising the step of:
separating the non-condensed portion of the overhead vapor from the hot side of the indirect heat exchanger into a methane stream and a stream of about 90 mole percent hydrogen, both the methane stream and 90 mole percent hydrogen stream being free of ethylene.

15. A process as in claim 14 further comprising the steps of:
passing the hydrogen stream through the cold side of the indirect heat exchanger;
passing the hydrogen stream issuing from the cold side of the indirect heat exchanger through an expansion turbine to cool the hydrogen stream; and
passing the expanded, cooled hydrogen stream through the cold side of the indirect heat exchanger.

16. A process as in claim 15 further comprising the steps of:
fractionally condensing the cracked gas serially in serveral stages to produce a vapor fraction of ethylene containing gas and an ethylene rich liquid fraction;
passing the methane stream through the cold side of the heat exchanger;
passing the hydrogen and methane streams discharging from the indirect heat exchanger in indirect heat exchange with the vapor fraction of ethylene containing gas from the fractional condensing step to further cool said vapor fraction; and delivering the cooled vapor fraction to the rectifier tower.

17. A process as in claim 16 further comprising the steps of:
   directing the ethylene rich liquid fraction from the fractional condenser system to a demethanizer; and
   delivering the bottoms product from the rectifier to the demethanizer whereby over 99 percent of the ethylene is recovered in the demethanizer.

18. A process as in claim 17 wherein the overhead vapor fraction from the fractional condenser is at about −144° F. when delivered to the rectifier tower; the overhead from the demethanizer is at about −151° F. when delivered to the rectifier tower; the rectifier tower is operated at approximately 392 psia; the overhead from the rectifier tower is approximately −203° F.; the reflux condensate is comprised of approximately 3 mole percent hydrogen; 97 mole percent methane and less than 0.1 percent ethylene; the non-condensed overhead is 75 percent hydrogen and 25 percent methane and is further cooled to −245° F. to produce a 90 mole percent hydrogen gas.

* * * * *